United States Patent
Kim et al.

(10) Patent No.: US 9,717,476 B2
(45) Date of Patent: Aug. 1, 2017

(54) PROBE AND MEDICAL IMAGING APPARATUS INCLUDING THE SAME

(71) Applicant: SAMSUNG ELECTRONICS CO., LTD., Suwon-si (KR)

(72) Inventors: Woon-bae Kim, Seoul (KR); Woo-young Jang, Seongnam-si (KR); Min-seog Choi, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 274 days.

(21) Appl. No.: 14/536,152

(22) Filed: Nov. 7, 2014

(65) Prior Publication Data
US 2015/0133775 A1 May 14, 2015

(30) Foreign Application Priority Data
Nov. 8, 2013 (KR) .......................... 10-2013-0135840

(51) Int. Cl.
*A61B 8/00* (2006.01)
*A61B 5/00* (2006.01)

(52) U.S. Cl.
CPC .......... *A61B 8/4444* (2013.01); *A61B 5/0066* (2013.01); *A61B 5/0084* (2013.01); *A61B 5/0095* (2013.01); *A61B 2560/04* (2013.01)

(58) Field of Classification Search
CPC . A61B 2560/04; A61B 5/0066; A61B 5/0084; A61B 5/0095; A61B 8/4444
See application file for complete search history.

(56) References Cited

U.S. PATENT DOCUMENTS

| | | | |
|---|---|---|---|
| 6,233,350 B1 * | 5/2001 | Mehrotra | G02B 27/0172 348/82 |
| 6,315,732 B1 | 11/2001 | Suorsa et al. | |
| 7,077,808 B2 | 7/2006 | Couvillon, Jr. | |
| 7,364,543 B2 | 4/2008 | Yang et al. | |
| 8,169,618 B2 | 5/2012 | Inoue | |
| 8,460,195 B2 | 6/2013 | Courtney et al. | |
| 2010/0292539 A1 | 11/2010 | Lankenau et al. | |
| 2011/0098572 A1 | 4/2011 | Chen et al. | |

* cited by examiner

*Primary Examiner* — Michael Rozanski
(74) *Attorney, Agent, or Firm* — Sughrue Mion, PLLC

(57) ABSTRACT

The probe includes a probe body that includes an internal empty space and is configured to be inserted into a coelom; an energy source module that is disposed in the probe body, and configured to emit an energy beam; first and second view windows that are provided at an end portion of the probe body, have different fields of view, and are configured to transmit the emitted energy beam; and a path changing unit that is disposed in the probe body, and configured to change a traveling path of the emitted energy beam to travel to one of the first view window and the second view window.

21 Claims, 11 Drawing Sheets

PROBE AND MEDICAL IMAGING APPARATUS INCLUDING THE SAME

CROSS-REFERENCE TO RELATED APPLICATION

This application claims priority from Korean Patent Application No. 10-2013-0135840, filed on Nov. 8, 2013, in the Korean Intellectual Property Office, the disclosure of which is incorporated herein in its entirety by reference.

BACKGROUND

1. Field

One or more exemplary embodiments relate to a probe and a medical imaging apparatus including the same, and more particularly, to a probe having an adjustable field of view and a medical imaging apparatus including the same.

2. Description of the Related Art

In the medical imaging field, the demand for information about a tissue (for example, of a human body or a skin) and for technology imaging a lower tomography is increasing. In particular, most of cancers occur under an epithelial cell, and metastasize to inside a hypodermal cell. Therefore, when it is possible to early detect cancer, a damage caused by the cancer is considerably reduced. A related art imaging technology using a magnetic resonance imaging (MRI) apparatus, a computed tomography (CT) apparatus, ultrasound, or the like images an internal tomography through a skin, but since a resolution is low, it is difficult to early detect small-size cancer.

On the other hand, recently proposed optical coherence tomography (OCT) technology, optical coherence microscopy (OCM) technology, and photoacoustic tomography (PAT) technology may use light to diagnose early stages of cancer. Although a skin penetration depth may be as low as 1 mm to 2 mm for the OCT technology or 50 mm to 50 mm for the PAT technology, a resolution is higher by about ten to twenty times than the ultrasound, and thus, these technologies may usefully diagnose incipient cancer.

The described-above medical imaging methods use a small-size probe receives light from a light source to transfer the light to inside a human body, for applying endoscope, celioscope, an surgical robot, and the like to the inside of the human body.

Probes are categorized into side-looking probes and forward-looking probes. For example, the side-looking probes are used to scan a narrow area such as a cardiovascular vessel, a throat, a large intestine, or the like, and the forward-looking probes are used to scan a broad part such as an eye, a skin, a digestive organ, or the like. However, the side-looking probes and the forward-looking probes have a limitation in that a field of view (FOV) is limited. Also, it is known that a three-dimensional (3D) forward-looking probe having a high resolution is more effective for chronic total occlusion or therapeutic than the side-looking probe. In addition, most of tissues are dependent on a directional angle of an ultrasound wave or light, and thus, a field of view is required to be adjusted. Therefore, the probe needs to be changed in accordance with a forward-looking operation or a scan-looking operation according to a looked object or a scan method, which is cumbersome and requires extra probes.

SUMMARY

Exemplary embodiments address at least the above problems and/or disadvantages and other disadvantages not described above. Also, the exemplary embodiments are not required to overcome the disadvantages described above, and may not overcome any of the problems described above.

One or more exemplary embodiments include a probe having an adjustable field of view, which changes a light path for using all of a side-looking type and a forward-looking type, and a medical imaging apparatus including the same.

According to one or more exemplary embodiments, a probe includes: a probe body that includes an internal empty space, and is inserted into a coelom; an energy source module that is disposed in the probe body, and emits an energy beam; first and second view windows that are provided at an end portion of the probe body, have different fields of view, and transmit the energy beam emitted from the energy source module; and a path changing unit that is disposed in the probe body, and changes a traveling path of the energy beam, emitted from the energy source module, to one of the first and second view windows.

The path changing unit may include: a slider that is movably disposed in the probe body; a reflective plate that includes a reflective surface reflecting the energy beam emitted from the energy source module, and is pivotably coupled to a distal end of the slider; and a guide member that restricts movement of the reflective plate according to movement of the slider to guide the reflective plate to one of a first arrangement, in which the traveling path of the energy beam emitted from the energy source module is changed to the first view window, and a second arrangement in which the traveling path of the energy beam emitted from the energy source module is changed to the second view window.

The energy source module may be disposed for the energy beam to be emitted to a front of the end portion of the probe body, the first view window may be disposed at a side surface of the end portion of the probe body, and the second view window is disposed at a front surface of the end portion of the probe body, the first arrangement of the reflective plate may be an arrangement in which the reflective plate is raised up to be inclined with respect to the slider, a reflective surface of the reflective plate reflects the energy beam, emitted from the energy source module, to the first view window, and the second arrangement of the reflective plate may be an arrangement in which the reflective plate is lowered down in parallel with the slider, and the energy beam emitted from the energy source module travels to the second view window without being reflected by the reflective plate.

The slider and the reflective plate may be coupled to each other by a hinge.

The guide member may include: a first guide member that is disposed at a rear surface of the reflective surface of the reflective plate, and guides the reflective plate to the first arrangement when the distal end of the slider moves in a first direction facing the end portion of the probe body; and a second guide member that is disposed at the reflective surface of the reflective plate, and guides the reflective plate to the second arrangement when the distal end of the slider moves in a second direction opposite to the first direction.

The path changing unit may include a loading unit that allows the reflective plate to be loaded in the first arrangement.

The slider and the reflective plate may be coupled to each other by an elastic member.

The slider, the reflective plate, and the elastic member may be provided as one body.

The reflective plate may be in the first arrangement due to elastic-restoring force with external force not being applied to the elastic member. When the distal end of the slider moves in a first direction facing the end portion of the probe, the guide member may expose the reflective plate with the external force not being applied thereto, and when the distal end of the slider moves in a second direction opposite to the first direction, the guide member may guide the reflective plate to the second arrangement.

The probe may further include a driver that is disposed inside or outside the probe body, and moves the slider.

The first and second view windows may be separated from each other, or are continuously provided.

The energy source module may include an optical fiber that transfers light, which is emitted from a light source disposed outside the probe body, to the end portion of the probe body.

Light emitted from the energy source module may be a pulse laser beam that induces an ultrasound wave from an object, and the energy source module may further include an ultrasound transducer that detects the ultrasound wave supplied from the object.

The energy source module may include an ultrasound transducer that converts an electrical signal into an ultrasound wave to emit the ultrasound wave, and detects an ultrasound wave reflected from an object.

According to one or more exemplary embodiments, a medical imaging apparatus includes: an energy source; a probe that emits energy beam, emitted from the energy source, onto an object; a controller that controls a path changing unit of the probe such that a traveling direction of the energy beam emitted from the probe is changed to one of first and second view windows; a receiver that receives a signal which is generated from the object by using the emitted energy beam; and a signal processor that processes the signal received by the receiver to generate an image signal, wherein the probe includes: a probe body that includes an internal empty space, and is inserted into a coelom; an energy source module that is disposed in the probe body, and emits the energy beam; the first and second view windows that are provided at an end portion of the probe body, have different fields of view, and transmit the energy beam emitted from the energy source module; and the path changing unit that is disposed in the probe body, and changes a traveling path of the energy beam, emitted from the energy source module, to one of the first and second view windows.

The energy source may include a light source that emits the light.

The signal processor may generate an endoscopic image by using the light reflected from the object.

The medical imaging apparatus may further include an optical coherence system that splits the light from the energy source to generate a reference beam and a measurement beam which is coherent light, wherein the signal processor may generate an optical coherence tomography image by using the measurement beam, reflected or scattered from the object, and the reference beam.

The light source may include a pulse laser that induces an ultrasound wave from the object, the receiver may convert the ultrasound wave, generated from the object, into an electrical signal, and the signal processor may generate a photoacoustic image by using the electrical signal.

The energy source and the receiver may be provided in the energy source module of the probe, and may include, in common, an ultrasound transducer that converts an electrical signal into an ultrasound wave to emit the ultrasound wave, and detects an ultrasound wave reflected from an object to convert the detected ultrasound wave into an electrical signal, and the signal processor may generate an ultrasound image by using the electrical signal.

BRIEF DESCRIPTION OF THE DRAWINGS

The above and/or other aspects will become more apparent by describing certain exemplary embodiments, with reference to the accompanying drawings, in which.

DETAILED DESCRIPTION

Figure 1:
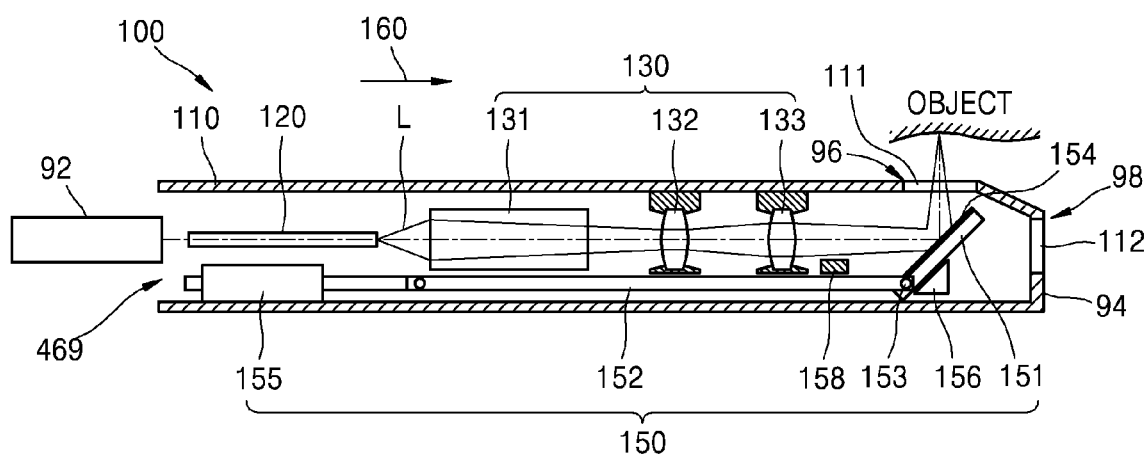
FIG. 1 is a cross-sectional view illustrating a schematic structure in a first arrangement of a probe according to an exemplary embodiment.

Certain exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

Expressions such as "at least one of," when preceding a list of elements, modify the entire list of elements and do not modify the individual elements of the list. In the drawings, the size of each element may be exaggerated for clarity and convenience of description.

Figure 2:
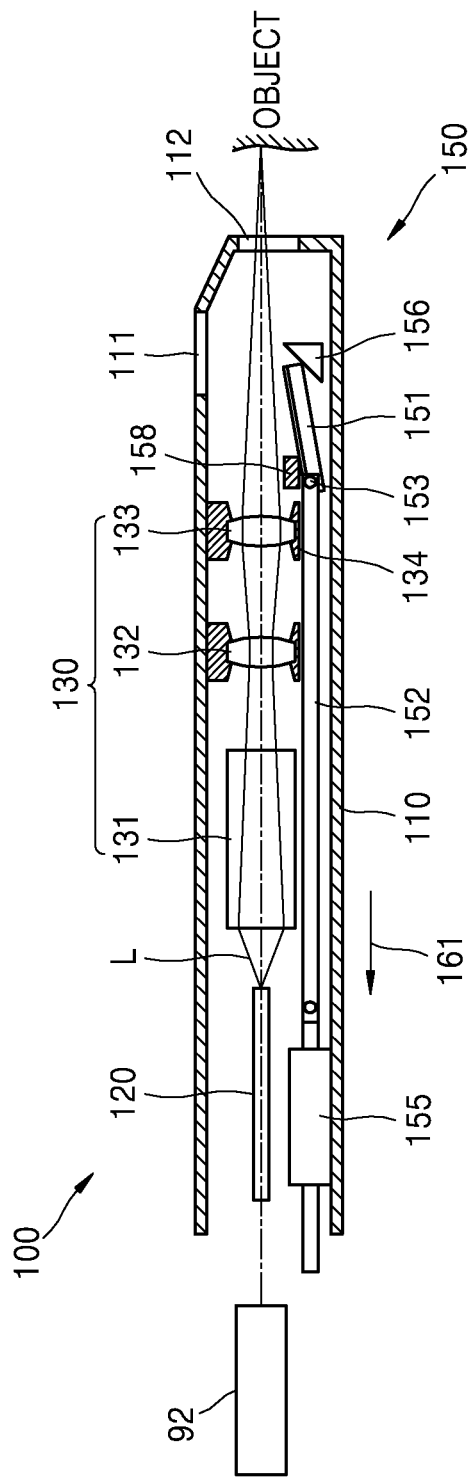
FIG. 2 is a cross-sectional view illustrating a schematic structure in a second arrangement of the probe of FIG. 1.

FIG. 1 is a cross-sectional view illustrating a schematic structure in a first arrangement of a probe 100 according to an exemplary embodiment, and FIG. 2 is a cross-sectional view illustrating a schematic structure in a second arrangement of the probe 100.

Referring to FIGS. 1 and 2, the probe 100 includes a probe body 110, an optical fiber 120 that is disposed in the probe body 110, and a path changing unit 150 that changes a traveling path of light L. The probe 100 may be an optical probe that emits the light L.

At least one portion of the probe body 110 may be a sheath that extends in a lengthwise direction so as to be inserted into a coelom. An empty space is provided in the probe body such that the optical fiber 120, an optical system 130, and the path changing unit 150 are disposed in the empty space. At least one portion of the probe body 110 may be formed of a flexible material. The probe body 110 may have, for example, a diameter of several mm. For example, when the probe 100 is used to scan a cardiovascular vessel, the diameter of the probe body 110 may be from about 1 mm to about 3 mm. A horizontal cross-sectional surface vertical to the lengthwise direction of the probe body 110 may have a circular shape, an oval shape, or a polygonal shape, but is not limited thereto. An end portion of the probe body 110 may have an angular shape, a tapered shape, or a hemispherical shape, but is not limited thereto.

First and second view windows 111 and 112 are provided at the end portion 98 of the probe body 110. The first view window 111 is disposed at a side surface 96 of the end portion of the probe body 110, and provides a side view. The second view window 112 is disposed at a front surface 94 of the end portion of the probe body 110, and provides a forward view. The first and second view windows 111 and 112 are each formed of a transparent material through which the light L emitted from the optical fiber 120 passes.

The optical fiber 120 transfers light (for example, visible light or coherent light), which is emitted from a light source 92 (also see 510 of FIGS. 11 and 610 of FIG. 12) provided outside the probe 100, to the end portion of the probe body 110. That is, a distal end emitting light of the optical fiber 120 is disposed to face a front of the end portion of the probe body 110. The optical fiber 120 transfers light, which is reflected from an object, to a receiver (see 550 of FIGS. 11 and 650 of FIG. 12) provided outside the probe 100.

The path changing unit 150 is an element that is disposed in the probe body 110, and changes a traveling path of the light, emitted from the optical fiber 120, to one of the first and second view windows 111 and 112. The path changing unit 150 includes a reflective plate 151, a slider 152, a driver 155 that drives the slider 152, and first and second guide members 156 and 158.

The reflective plate 151 is pivotably coupled to a distal end of the slider 152. For example, as illustrated in FIG. 1, the reflective plate 151 and the slider 152 may be coupled to each other in a hinge structure having a pivotal shaft 153. One surface of the reflective plate 151 is a reflective surface 154 that reflects the light emitted from the optical fiber 120.

The slider 152 is movably disposed in the lengthwise direction of the probe body 110.

The driver 155 may be a linear motor that is connected to the other end of the slider 152, and moves the slider 152 forward or backward, in the lengthwise direction. For example, the driver 155 may be an ultrasound motor or any other appropriate motor.

FIG. 1 illustrates the first arrangement of the reflective plate 151, and FIG. 2 illustrates the second arrangement of the reflective plate 151. The first arrangement of the reflective plate 151 is an arrangement in which the reflective surface 154 of the reflective plate 151 is raised up to be inclined with respect to a lengthwise direction of the slider 152 so as to reflect the light, emitted from the distal end of the optical fiber 120, to the first view window 111. The second arrangement of the reflective plate 151 is an arrangement in which the reflective surface 154 of the reflective plate 151 is lowered down to be disposed substantially parallel with the lengthwise direction of the slider 152 such that the light emitted from the distal end of the optical fiber 120 directly travels to the second view window 112 without being reflected by the reflective plate 151.

The first guide member 156 is disposed at a rear surface of the reflective plate 151, and guides the reflective plate 151 to the first arrangement when the distal end of the slider 152 moves in a first direction 160 toward the end portion of the probe body 110. For example, the first guide member 156 has an oblique surface opposite to the rear surface of the reflective surface 154 of the reflective plate 151, and in the first arrangement, the rear surface of the reflective surface 154 of the reflective plate 151 may contact the oblique surface of the first guide member 156.

The second guide member 158 is disposed proximate a front surface of the reflective surface 154 of the reflective plate 151, and when the distal end of the slider 152 moves in a second direction 161 opposite to the first direction 160, the second guide member 158 guides the reflective plate 151 to the second arrangement.

The second guide member 158 may have a guide function of guiding movement in the lengthwise direction of the slider 152. For example, a shape of a guide member 253 to be described below with reference to FIG. 7 may be applied to the second guide member 158. Alternatively, the second guide member 158 may be provided as one body with a lens holder 134 of lenses 131, 132, and/or 133 of the optical system 130 provided in the probe body 110, or may be provided as one body with the other mechanical element of the probe body 110.

Each of the first and second guide members 156 and 158 is an example of a guide member that restricts movement of the reflective plate 151 according to movement of the slider 152 to guide the reflective plate 151 to the first or second arrangement, and a detailed shape of each of the first and second guide members 156 and 158 may be variously modified.

The path changing unit 150 has a very simple structure, and, thus, even when the diameter of the probe body 110 is several mm, the path changing unit 150 may be disposed in an internal space of the probe body 110.

The optical system 130 may be provided between the distal end of the optical fiber 120 and the reflective plate 151. The optical system 130 condenses and emits the light emitted from the optical fiber 120 onto an object of the coelom. The optical system 130 may condense light reflected by the object of the coelom to be incident onto the optical fiber 120. The optical system 130 may include a collimating lens 131 that shapes the light, emitted from the optical fiber 120, at a parallel light pencil. The collimating lens 131 may be a graded index (GRIN) lens, a spherical lens, or an aspherical lens. The optical system 130 may further include a plurality of condensing lenses 132 and 133 that condense the light. The lenses 131 to 133 of the optical system 130 are fixed to the probe body 110 by the lens holder or holders 134. A configuration of the optical system 130 may be appropriately designed depending on a characteristic of the light L emitted from the optical fiber 120 or a characteristic of the object.

The probe 100 may selectively provide a side view and a forward view.

When desiring to set the probe 100 to the side view, as illustrated in FIG. 1, the reflective plate 151 is set in the first arrangement. That is, the driver 155 moves the slider 152 in the first direction 160 corresponding to the end portion of the probe body 110, and, thus, the slider 152 pushes the reflective plate 151 in the first direction 160 of the probe body 110. The pushed reflective plate 151 is raised up along the oblique surface of the first guide member 156. The light L emitted from the optical fiber 120 is condensed by the optical system 130, reflected by the reflective plate 151, emitted to a side of the probe body 110 through the first view window 111, and emitted onto the object. The light L reflected by the object is input to inside the probe body 110 through the first view window 111, and travels in a reverse direction to enter the optical fiber 120.

When desiring to set the probe 100 to the forward view, as illustrated in FIG. 2, the reflective plate 151 is set in the second arrangement. That is, the driver 155 moves the slider 152 in the second direction 161 opposite to the end portion 98 of the probe body 110, and thus, the slider 152 pulls the reflective plate 151 in the second direction 161 of the probe body 110. The pulled reflective plate 151 deviates from the oblique surface of the first guide member 156, and is pressed down by the second guide member 158, and thus is substantially in a state parallel with the slider 152. The light L emitted from the optical fiber 120 is condensed by the optical system 130, emitted to a front of the probe body 110 through the second view window 112 without being reflected by the reflective plate 151, and emitted onto the object. The light L reflected by the object is input to inside the probe body 110 through the second view window 112, and then, the light L travels in a reverse direction, and enters the optical fiber 120.

For example, the side view is useful to scan a narrow part such as a cardiovascular vessel, a throat, a large intestine, or the like, and the forward view is useful to scan a broad part such as an eye, a skin, a digestive organ, or the like. Therefore, the side view and the forward view are selectively set depending on an object. The probe 100 may be inserted into the coelom while looking at a front of the distal end of the probe 100. Thus, even when an object is observed through the side view, the probe 100 may be set to a mode of providing the forward view in a process of inserting the probe 100 into the coelom, and when the distal end of the probe 100 reaches an object of the coelom which is to be observed, the probe 100 may be changed to a mode of providing the side view.

Figure 3:
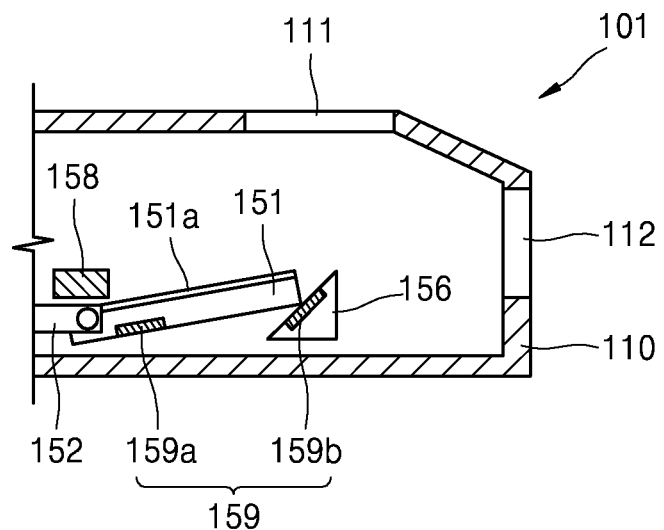
FIGS. 3 and 4 are cross-sectional views illustrating a schematic structure of an end portion of a probe according to an exemplary embodiment.
Figure 4:
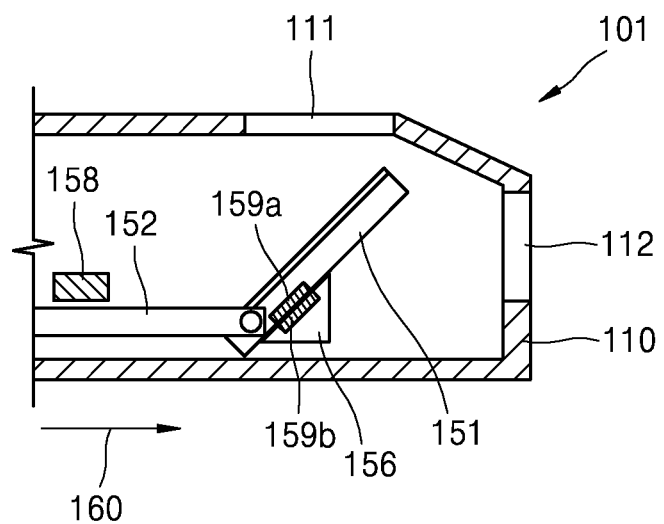

FIGS. 3 and 4 are cross-sectional views illustrating a schematic structure of an end portion of a probe 101 according to an exemplary embodiment. Referring to FIGS. 3 and 4, the probe 101 according to the present exemplary embodiment further includes a loading unit 159 that allows the reflective plate 151 to be loaded, i.e., erected, in the first arrangement.

The loading unit 159 may include a first loading member 159a, which is provided at the rear surface of the reflective surface 154 of the reflective plate 151, and a second loading member 159b that is provided at the oblique surface of the first guide member 156. The first and second loading members 159a and 159b are disposed to contact each other when the reflective plate 151 is in the first arrangement as illustrated in FIG. 4. The first and second loading members 159a and 159b may be permanent magnets of which opposite surfaces have opposite polarities. Therefore, when the slider 152 pushes the reflective plate 151 in the first direction, the first loading member 159a of the reflective plate 151 approaches the second loading member 159b, and the first and second loading members 159a and 159b are affixed to each other by magnetic attractive force, whereby the reflective plate 151 is disposed at an accurate position in the first arrangement.

The loading unit 159 is only an example, and is not limited thereto. For example, the loading unit 159 may other appropriate means that guides a position as in a groove or a projection that is provided at the rear surface of the reflective surface 154 of the reflective plate 151 or the oblique surface of the first guide member 156.

Except that the probe 101 further includes the loading unit 159 which allows the reflective plate 151 to be loaded in the first arrangement, the probe 101 according to the present exemplary embodiment is substantially the same as the probe 100 described above with reference to FIGS. 1 and 2, and thus, the other elements except the loading unit 159 are not described.

Figure 5:
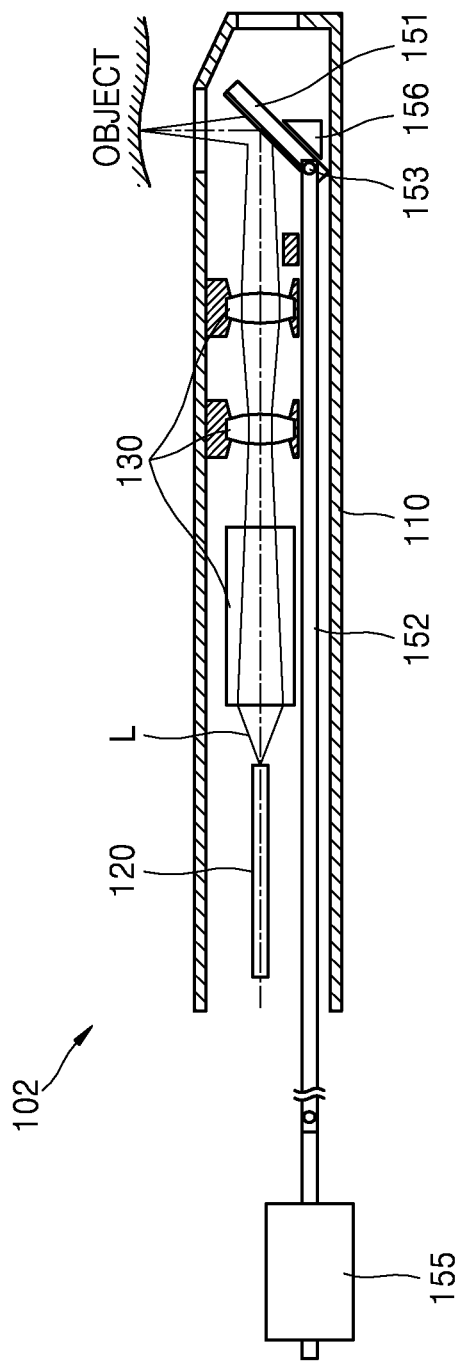
FIG. 5 is a cross-sectional view illustrating a schematic structure of a probe according to an exemplary embodiment.

In the probe 100 described above with reference to FIGS. 1 and 2, a case in which the driver 155 is disposed in the probe body 110 is described as an example, but is not limited thereto. FIG. 5 is a cross-sectional view illustrating a schematic structure of a probe 102 according to an exemplary embodiment. As illustrated in FIG. 5, in the probe 102 according to the present exemplary embodiment, the driver 155 may be disposed outside the probe body 110. Since the driver 155 is disposed outside the probe body 110, the diameter size of the probe body 110 is more reduced, and moreover, the driver 155 may be more variously selected without being limited in size. Except that the driver 155 is disposed outside the probe body 110, the probe 102 according to the present exemplary embodiment is substantially the same as the probe 100 described above with reference to FIGS. 1 and 2, and thus, the other elements except the driver 155 are not described.

Figure 6:
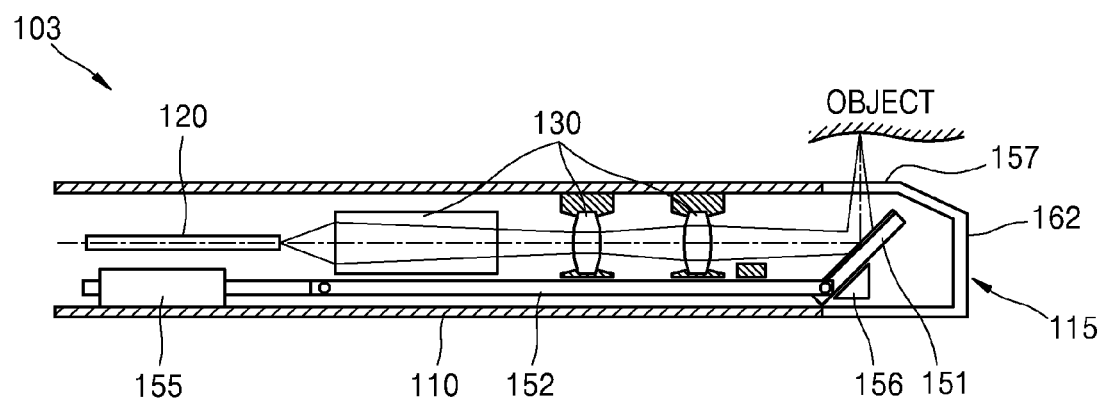
FIG. 6 is a cross-sectional view illustrating a schematic structure of a probe according to an exemplary embodiment.

In the probe 100 described above with reference to FIGS. 1 and 2, the first and second view windows 111 and 112 are formed to be separated from each other, but are not limited thereto. FIG. 6 is a cross-sectional view illustrating a schematic structure of a probe 103 according to an exemplary embodiment. As illustrated in FIG. 6, in the probe 103 according to an exemplary embodiment, the view window 115 may be continuously formed at a front surface and a side surface of the end portion of the probe body 110. In this case, one side surface 157 of the view window 115 may correspond to the first view window 111 according to the above-described exemplary embodiment, and a front surface 162 of the view window 115 may correspond to the second view window 112 according to the above-described exemplary embodiment. Since the view window 115 is continuously formed, the probe 102 may provide a continuous expanded field of view.

In the probes 100 to 102 described above with reference to FIGS. 1 to 6, a structure in which the reflective plate 151 and slider 152 of the path changing unit 150 is described as an example, but is not limited thereto. As an example, a probe 200 according to an embodiment uses an elastic member as a path changing unit 250.

Figure 7:
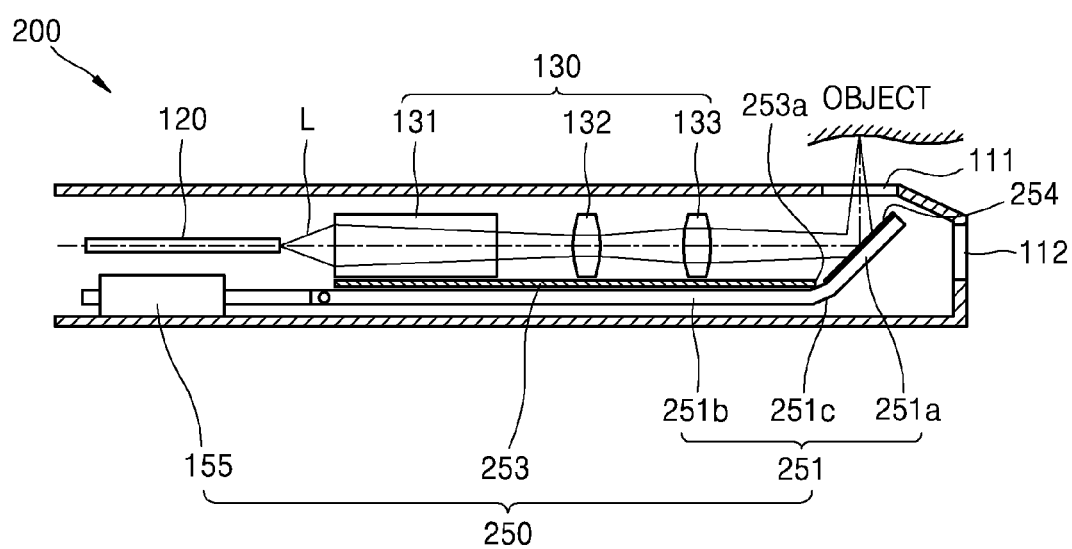
FIG. 7 is a cross-sectional view illustrating a schematic structure in a first arrangement of a probe according to an exemplary embodiment.
Figure 8:
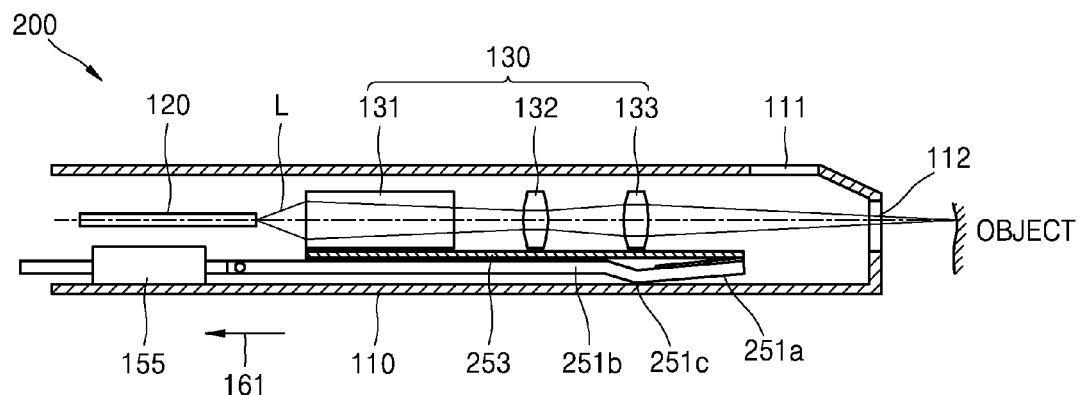
FIG. 8 is a cross-sectional view illustrating a schematic structure in a second arrangement of the probe of FIG. 7.

FIG. 7 is a cross-sectional view illustrating a schematic structure in a first arrangement of the probe 200 according to an exemplary embodiment, and FIG. 8 is a cross-sectional view illustrating a schematic structure in a second arrangement of the probe 200 of FIG. 7.

Referring to FIGS. 7 and 8, the probe 200 according to the present exemplary embodiment includes the probe body 110, the optical fiber 120 that is disposed in the probe body 110, and the path changing unit 250 that changes the traveling path of the light L. Except for a configuration of the path changing unit 250, the probe 200 according to the present exemplary embodiment is substantially the same as the probe 100 described above with reference to FIGS. 1 and 2, and thus, the other elements except the path changing unit 250 are not described.

The path changing unit 250 includes a leaf spring 251 including a reflective surface 254, the driver 155 that drives the leaf spring 251, and a guide member 253.

The leaf spring 251 may be provided as one body comprising a reflective plate 251a, a slider 251b, and a connection part 251c. The reflective plate 251a may be understood as a region in which the reflective surface 254 is disposed in the leaf spring 251. In the leaf spring 251, the driver 155 is connected to an end portion of the slider 251b, and thus, the slider 251b is movably disposed in the lengthwise direction of the probe body 110.

In the leaf spring 251, the connection part 251c may be bent without external force being applied thereto, and thus, the reflective plate 251a may be in the first arrangement. The first arrangement of the reflective plate 251a, as illustrated in FIG. 7, is an arrangement in which the reflective surface 254 of the reflective plate 251a is raised up to be inclined with respect to a lengthwise direction of the slider 251b so as to reflect the light, emitted from the distal end of the optical fiber 120, to the first view window 111. On the other hand, when external force is applied, the leaf spring 251 may have a shape in which the connection part 251c is spread, and thus, the reflective plate 251a is in the second arrangement. The second arrangement of the reflective plate 251a, as illustrated in FIG. 8, is an arrangement in which the reflective surface 254 of the reflective plate 251a is lowered down in parallel with the lengthwise direction of the slider 251b such that the light emitted from the distal end of the optical fiber 120 directly travels to the second view window 112 without being reflected by the reflective plate 151.

The guide member 253 accommodates the slider 251b in an inner portion thereof to guide movement of the slider 251b, and when the reflective plate 251a moves in the second direction 161 opposite to the first direction 160, an accommodating space for accommodating the slider 251b and the reflective plate 251a in the inner portion is provided. Therefore, when the reflective plate 251a moves in the first direction 160, the guide member 253 exposes the reflective plate 251a with external force not being applied thereto, and thus, the reflective plate 251a is in the first arrangement due to elastic-restoring force. On the other hand, when the reflective plate 251a moves in the second direction 161 opposite to the first direction 160, the guide member 253 constrains the reflective plate 251a into an inner portion of the guide member 23 to guide the reflective plate 251a to the second arrangement.

The guide member 253 may be provided as one body with the lens holder 134 of each of the lenses 131 to 133 of the optical system 130 provided in the probe body 110, or may be provided as one body with the other mechanical structure of the probe body 110.

The guide member 253 is an example of a guide member that restricts movement of the reflective plate 251a according to movement of the slider 251b to guide the reflective plate 151 to one of the first and second arrangements, and a detailed shape of the guide member 253 may be variously modified.

The path changing unit 250 has a very simple structure, and thus, even when the diameter of the probe body 110 is several mm, the path changing unit 250 may be disposed in an internal space of the probe body 110.

In according to the present exemplary embodiment, a case in which the reflective plate 251a and the slider 251b configure a one-body leaf spring is described, but an exemplary embodiment is not limited thereto. For example, the reflective plate 251a and the slider 251b are the same as the reflective plate 151 and slider 152 of the probe 100 described above with reference to FIGS. 1 and 2, respectively, and the reflective plate 251a and the slider 251b may be connected to each other by an elastic member.

Figure 9:
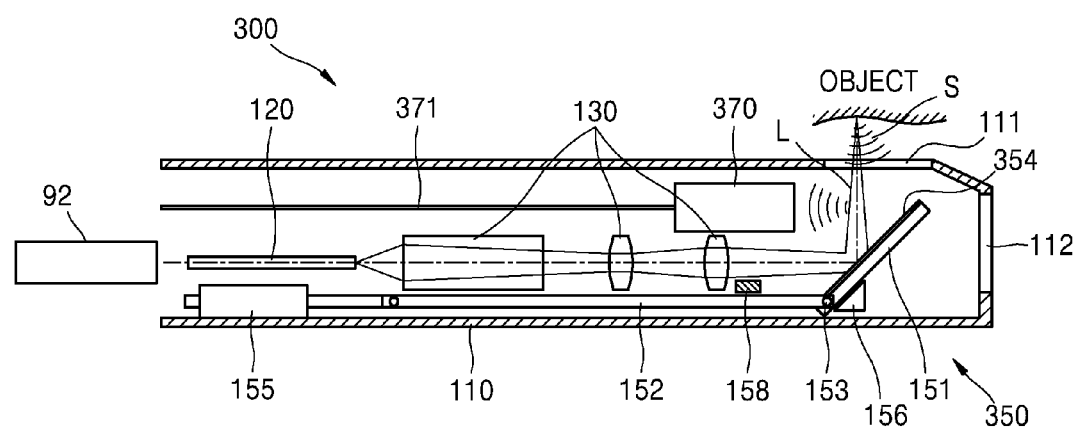
FIG. 9 is a cross-sectional view illustrating a schematic structure of a probe according to an exemplary embodiment.

FIG. 9 is a cross-sectional view illustrating a schematic structure of a probe 300 according to an exemplary embodiment.

Referring to FIG. 9, the probe 300 according to the present exemplary embodiment includes the probe body 110, the optical fiber 120 that is disposed in the probe body 110, the path changing unit 350 that changes the traveling path of the light L, and an ultrasound transducer 370 that detects an ultrasound wave supplied from an object. Except for a configuration of the path changing unit 350, the probe 300 according to the present exemplary embodiment is substantially the same as the probe 100 described above with reference to FIGS. 1 and 2, and thus, the other elements except the path changing unit 250 are not described. The probe 300 may be a photoacoustic tomography (PAT) probe that emits a laser beam onto the object, and receives the ultrasound wave supplied from the object. PAT is technology that emits a laser pulse into a cell tissue (an object), and detects a pressure wave generated from the cell tissue to generate an image. When a laser beam is emitted onto a liquid or solid material, the liquid or solid material receiving the laser beam absorbs optical energy to generate momentary thermal energy, which generates an acoustic wave due to a thermoelastic phenomenon. Since an absorption rate and a thermoelastic coefficient based on a wavelength of light are changed according to a material forming an object, ultrasound waves having different intensities are generated from the same optical energy. By detecting the ultrasound waves, a distribution of blood vessels and a characteristic change of a fine tissue in a human body may be realized as images by a non-invasive method.

The optical fiber 120 transfers a pulse laser beam, emitted from a light source 92 (see also 710 of FIG. 13) provided outside the probe 300, to the end portion of the probe body 110. However, the optical fiber 120 according to the present exemplary embodiment does not receive light supplied from the object, and thus, the optical fiber 120 may be used for only emitting light. Depending on the case, instead of the optical fiber or along with the optical fiber 120, a laser diode emitting the pulse laser beam may be directly provided in the probe body 110.

The ultrasound transducer 370 may be disposed in parallel with the optical system 130 or the optical fiber 120, and may convert the ultrasound wave, supplied from the object, into an electrical signal. The ultrasound transducer 370 may be a piezoelectric micromachined ultrasound transducer (pMUT) that converts vibration, caused by the ultrasound wave, into the electrical signal. The pMUT may be formed of piezoelectric ceramic showing a piezoelectric phenomenon, a single crystalline material, and a complex piezoelectric material produced by combining the materials and a polymer. A plurality of piezoelectric elements configuring the ultrasound transducer 370 may be arranged one-dimensionally or two-dimensionally. As another example, the ultrasound transducer 370 may be implemented as a capacitive micromachined ultrasound transducer (cMUT), a magnetic micromachined ultrasound transducer (mMUT), or an optical ultrasound detector.

The path changing unit 350, as described above with reference to FIGS. 1 and 2, may include the reflective plate 151, the slider 152, the driver 155 driving the slider 152, the first guide member 156, and the second guide member 158. Alternatively, the path changing unit 350 may have the structure which is as described above with reference to FIGS. 7 and 8. However, there is a difference between the present exemplary embodiment and the above-described exemplary embodiments in that a reflective surface 354 provided on the reflective plate 151 reflects all of the pulse laser beam emitted from the optical fiber 120 and the ultrasound wave supplied from the object.

As in the above-described exemplary embodiments, when the probe 300 is to provide the side view, the reflective plate 151 is in the first arrangement, the pulse laser beam emitted from the optical fiber 110 is reflected by the reflective surface 354 of the reflective plate 151 and emitted through the first view window 111 onto an object located at a side, and an ultrasound wave generated from the object located at the side is input through the first view window 111, reflected by the reflective surface 354 of the reflective plate 151, and detected by the ultrasound transducer 370. When the probe 300 is to provide the forward view, the reflective plate 151 is in the second arrangement, the pulse laser beam emitted from the optical fiber 110 travels forward without being reflected by the reflective plate 151 to thereby be emitted through the second view window 112 onto an object located at a front, and an ultrasound wave generated from the object located at the front is input through the second view window 112, travels forward without being reflected by the reflective plate 151, and is detected by the ultrasound transducer 370.

Figure 10:
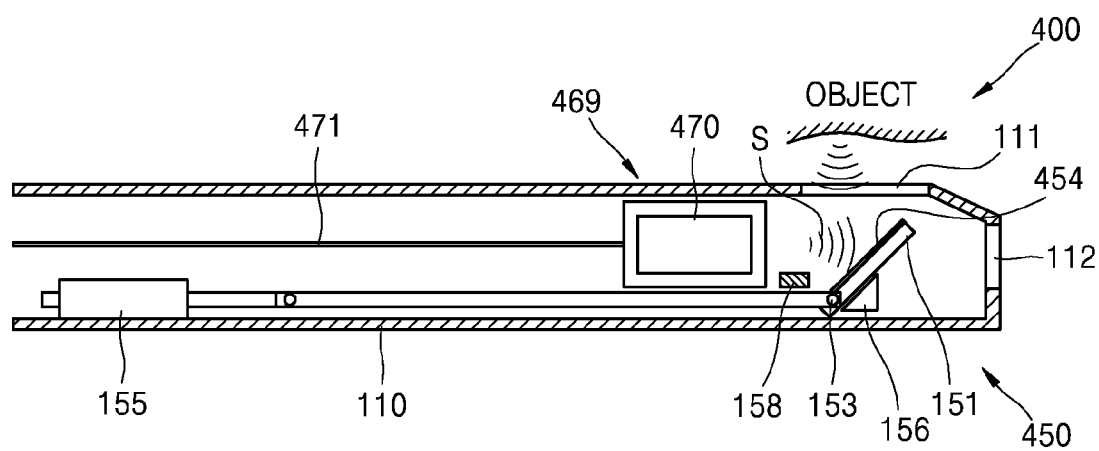
FIG. 10 is a cross-sectional view illustrating a schematic structure of a probe according to an exemplary embodiment.

FIG. 10 is a cross-sectional view illustrating a schematic structure of a probe 400 according to an exemplary embodiment.

The probe 400 according to an exemplary embodiment may be an ultrasound probe in which an energy source module emits an ultrasound wave. That is, the energy source module 469 may include an ultrasound transducer 470 that converts an electrical signal into an ultrasound wave to emit the ultrasound wave, and detects the ultrasound wave reflected by an object.

Referring to FIG. 10, the probe 400 includes the probe body 110, an ultrasound transducer 470 that is disposed in the probe body 110, and a path changing unit 450 that changes a traveling path of an ultrasound wave. The probe 400 may be the ultrasound probe that transmits an ultrasound wave to an object, and detects the ultrasound wave supplied from the object.

The probe body 110 and the path changing unit 450 are substantially the same as the probe body and the path changing unit according to the above-described exemplary embodiments, and thus, the repeated description will be omitted.

The ultrasound transducer 470 converts an electrical signal into an ultrasound wave, and converts an ultrasound wave, supplied from the object, into an electrical signal. Similarly to the ultrasound transducer 370 according to the above-described exemplary embodiment, the ultrasound transducer 470 may be implemented as the pMUT, the cMUT, the mMUT, or the optical ultrasound detector.

The path changing unit 450, as described above with reference to FIGS. 1 and 2, may include the reflective plate 151, the slider 152, the driver 155 driving the slider 152, the first guide member 156, and the second guide member 158. Alternatively, the path changing unit 450 may have the structure which is as described above with reference to FIGS. 7 and 8. However, there is a difference between the present exemplary embodiment and the above-described exemplary embodiments in that a reflective surface 454 provided on the reflective plate 151 reflects all of the ultrasound emitted from the ultrasound transducer 470 and the ultrasound wave supplied from the object.

As in the above-described exemplary embodiments, when the probe 400 is to provide the side view, the reflective plate 151 is in the first arrangement, the ultrasound emitted from the ultrasound transducer 470 is reflected by the reflective surface 454 of the reflective plate 151 and emitted through the first view window 111 onto an object located at a side, and an ultrasound wave generated from the object located at the side is input through the first view window 111, reflected by the reflective surface 454 of the reflective plate 151, and detected by the ultrasound transducer 470. When the probe 300 is to provide the forward view, the reflective plate 151 is in the second arrangement, the ultrasound emitted from the ultrasound transducer 470 travels forward without being reflected by the reflective plate 151 to thereby be emitted through the second view window 112 onto an object located at a front, and an ultrasound wave generated from the object located at the front is input through the second view window 112, travels forward without being reflected by the reflective plate 151, and is detected by the ultrasound transducer 470.

Figure 11:
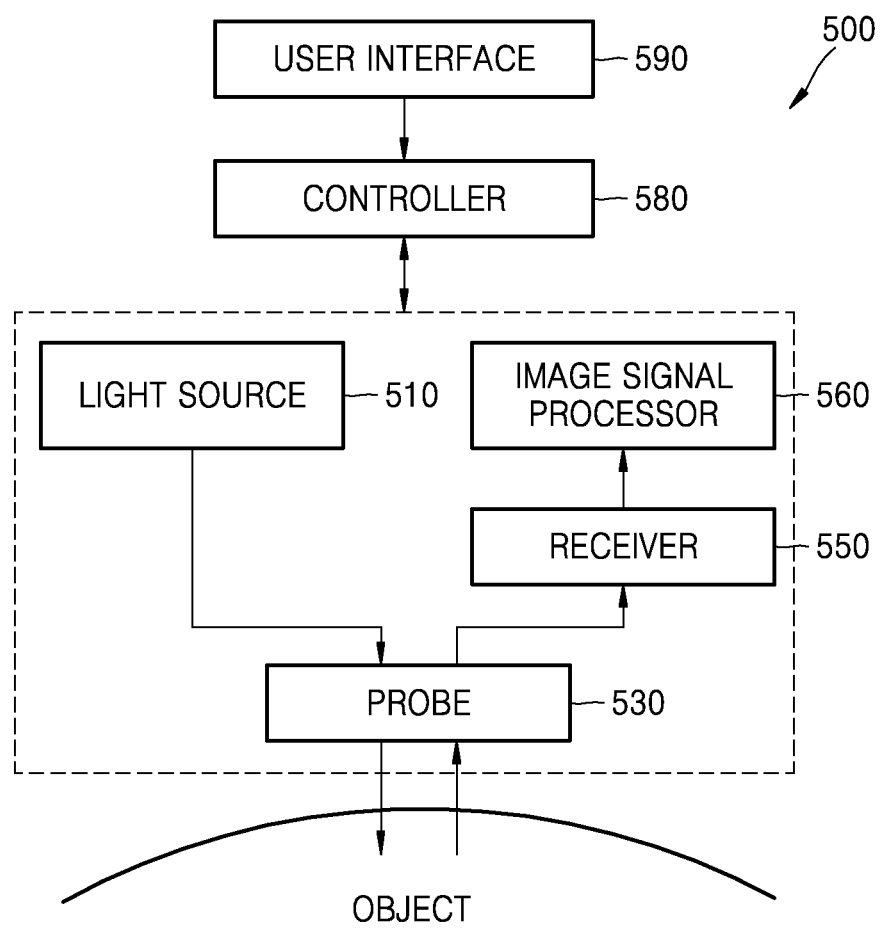
FIG. 11 is a block diagram illustrating a schematic configuration of a medical imaging apparatus according to an exemplary embodiment.

FIG. 11 is a block diagram illustrating a schematic configuration of a medical imaging apparatus 500 according to an exemplary embodiment. The medical imaging apparatus 500 according to the present exemplary embodiment is an example of an endoscopic imaging apparatus that generates an endoscopic image.

Referring to FIG. 11, the medical imaging apparatus 500 according to the present exemplary embodiment includes a light source 510, a probe 530 that emits light emitted from the light source 510 onto an object, a receiver 550 that receives a signal generated by the object, an image signal processor 560 that processes the signal received from the receiver 550 to generate an image signal, and a controller 580 that controls the probe 530.

The light source 510 emits illumination light (visible light), and may use a lamp, a semiconductor light-emitting device, or the like.

The probe 530 includes an element for emitting the illumination light onto the object, and, for example, may use one of the above-described probes 100, 101, 102 and/or 200.

Reflection light reflected from the object travels the receiver 550 through an optical fiber of the probe 530, and the receiver 550 phases the reflection light to acquire an image signal.

The image signal processor 560 generates the endoscopic image by using the reflection light that is reflected and received from the object.

Moreover, the medical imaging apparatus 500 may further include a user interface 590. The user interface 590 may include an input unit and a display, and may transfer a desired input to the controller 580 by using the input unit and the display.

The controller 580 controls the elements of the medical imaging apparatus 500 according to a command input from the user interface 590. For example, the controller 580 may control the path changing unit (150 of FIG. 1 or 250 of FIG. 7) to control a field of view of the probe 530. The controller 580 may be implemented with a microprocessor.

Figure 12:
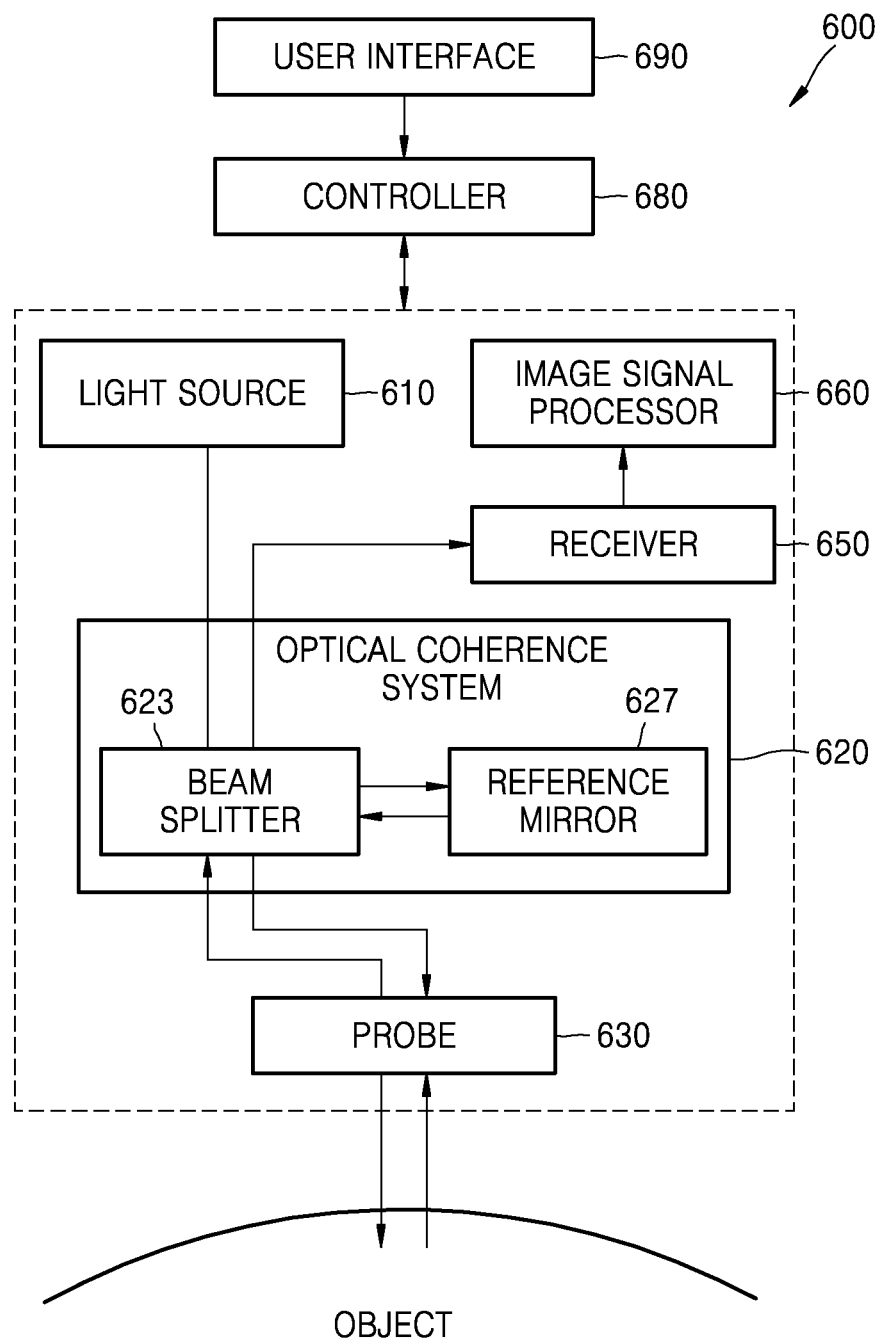
FIG. 12 is a block diagram illustrating a schematic configuration of a medical imaging apparatus according to an exemplary embodiment.

FIG. 12 is a block diagram illustrating a schematic configuration of a medical imaging apparatus 600 according to an exemplary embodiment. The medical imaging apparatus 600 is an example of using an optical coherence tomography (OCT).

Referring to FIG. 12, the medical imaging apparatus 600 according to the present exemplary embodiment includes a light source 610, a probe 630 that emits light emitted from the light source 610 onto an object, a receiver 650 that receives a signal generated from the object, an image signal processor 660 that processes the signal received from the receiver 650 to generate an image signal, and a controller 680 that controls the probe 530.

The light source 610 may include a laser diode that emits coherent light (i.e., a laser beam).

The medical imaging apparatus 600 may further include an optical coherence system 620 that splits light from the light source 610 to generate a reference beam and a measurement beam which is coherent light. The optical coherence system 620 includes a reference mirror 627 and a beam splitter 623. The light emitted from the light source 610 is partially split by the beam splitter 623, and is emitted onto and reflected from the reference mirror 627. That is, the coherent light generated by an interaction between the reference mirror 627 and the beam splitter 623 is used as the measurement beam, and is incident onto the probe 630. Such coherent light is generally used in an OCT mode.

The probe 630 may scan a certain region of the object and emit light onto the object, and, for example, may use one of the above-described probes 100, 101, 102 and/or 200.

The measurement beam reflected or scattered from the object is split by the beam splitter 623, and travels to the receiver 650. The image signal processor 660 generates an OCT image by using the measurement beam, reflected or scattered from the object, and the reference beam.

Moreover, the medical imaging apparatus 600 may further include a user interface 690. The user interface 690 may include an input unit and a display, and may transfer a desired input to the controller 680 by using the input unit and the display.

The controller 680 controls the elements of the medical imaging apparatus 600 according to a command input from the user interface 690. For example, the controller 680 may control the path changing unit (150 of FIG. 1 or 250 of FIG. 7) of the probe 630.

Figure 13:
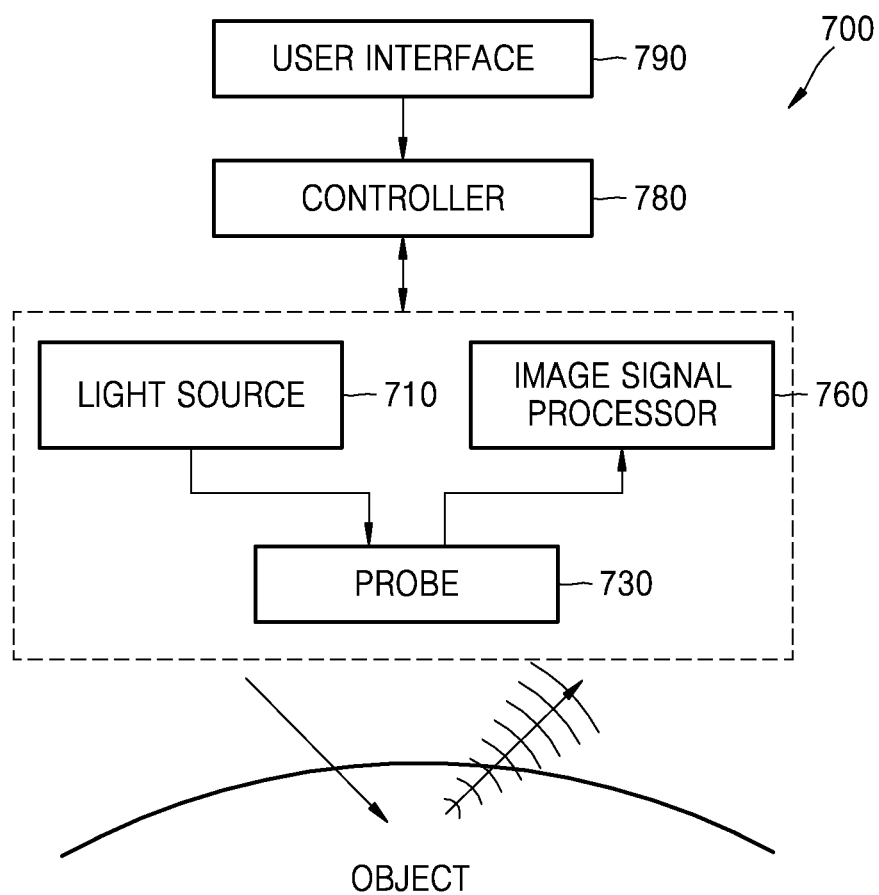
FIG. 13 is a block diagram illustrating a schematic configuration of a medical imaging apparatus according to an exemplary embodiment.

FIG. 13 is a block diagram illustrating a schematic configuration of a medical imaging apparatus 700 according to an exemplary embodiment. The medical imaging apparatus 700 is an example of using the PAT.

Referring to FIG. 13, the medical imaging apparatus 700 according to the present exemplary embodiment includes a light source 710, a probe 730 that emits light emitted from the light source 710 onto an object, a receiver 750 that receives a signal generated from the object, an image signal processor 760 that processes the signal received from the receiver 750 to generate an image signal, and a controller 780 that controls the probe 730.

The light source 710 may include a pulse laser that induces an ultrasound wave from the object, and a pulse width may be from about several picoseconds to about several nanoseconds.

The probe 730 may scan a certain region of the object and emit light onto the object, and, for example, may use the probe 300 described above with reference to FIG. 9.

When the probe 730 emits light onto the object, an ultrasound wave is generated from the object. The ultrasound wave generated from the object is received by the ultrasound transducer (370 of FIG. 9) included in the probe 730. Ultrasound waves having different frequency bands or intensities are generated depending on a pulse width and a pulse fluence of a laser beam and a laser absorption coefficient, a laser reflection coefficient, specific heat, and a thermal expansion coefficient of the object. That is, when a pulse laser is emitted onto the object, an ultrasound wave based on the kind of the object is generated, and by detecting the ultrasound wave, an image for determining the kind of the object is acquired.

The image signal processor 760 may process a signal received from the probe 730 to generate an ultrasound image.

Moreover, the medical imaging apparatus 700 may further include a user interface 790. The user interface 790 may include an input unit and a display, and may transfer a desired input to the controller 780 by using the input unit and the display.

The controller 780 controls the elements of the medical imaging apparatus 700 according to a command input from the user interface 790. For example, the controller 780 may control the path changing unit (350 of FIG. 9) of the probe 730.

Figure 14:
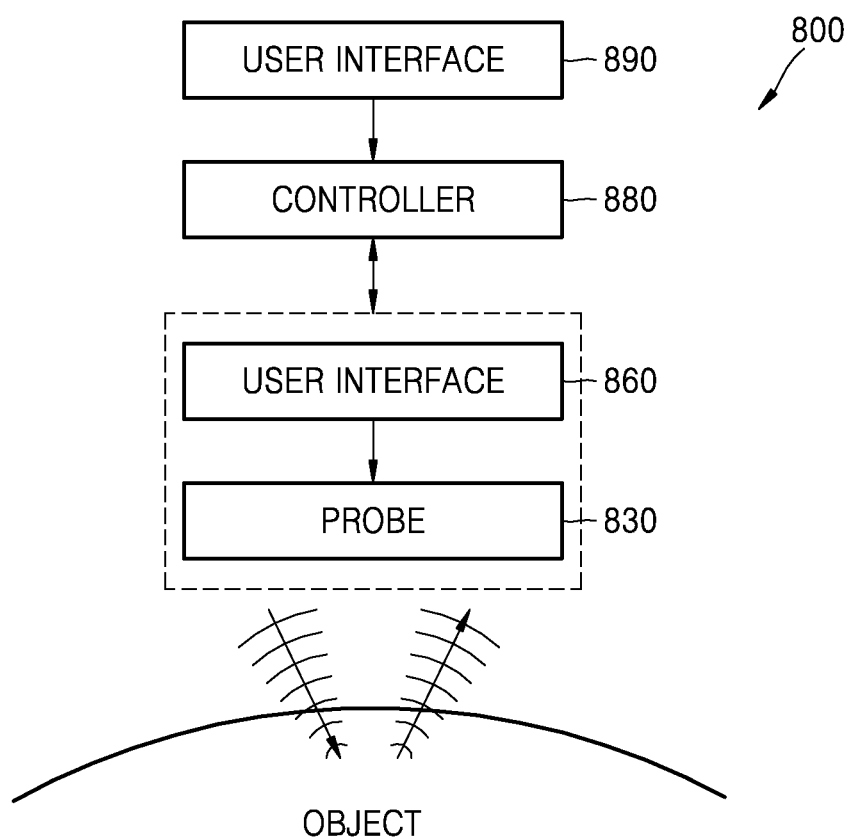
FIG. 14 is a block diagram illustrating a schematic configuration of a medical imaging apparatus according to an exemplary embodiment.

FIG. 14 is a block diagram illustrating a schematic configuration of a medical imaging apparatus 800 according to an exemplary embodiment. The medical imaging apparatus 800 is an example of an ultrasound imaging apparatus that generates an ultrasound image.

Referring to FIG. 14, the medical imaging apparatus 800 according to the present exemplary embodiment includes a probe 830, an image signal processor 860 that processes an ultrasound signal received from the probe 830 to generate an ultrasound image, and a controller 880 that controls the probe 830.

The probe 830 may scan a certain region of the object and emit ultrasound onto the object, and, for example, may use the probe 400 described above with reference to FIG. 10. The image signal processor 860 may process the ultrasound signal received from the probe 830 to generate the ultrasound image. The medical imaging apparatus 800 may further include a user interface 890. The user interface 890 may include an input unit and a display, and may transfer a desired input to the controller 880 by using the input unit and the display. In addition, the controller 880 controls the elements of the medical imaging apparatus 800 according to a command input from the user interface 890. For example, the controller 880 may control the path changing unit (450 of FIG. 10) of the probe 830.

The probes 100, 101, 102, 200, 300 and 400 are described above with reference to a case in which the first and second views are selectively changed by the path changing units 150, 250, 350 and 450, but this is not limiting. The probe may include a continuous view window, and may adjust a field of view according to a degree of movement of the slider. The path changing unit of the probe may additionally scan light at a selected field of view. Alternatively, the probe may further include an optical scan device (or an optical scan unit) that scans light one-dimensionally or two-dimensionally, and the optical scan device may scan light without changing a position or a field of view of the probe itself.

In the descriptions of the medical imaging apparatuses 600, 700, 800 and 900 according to the above-described exemplary embodiments, a configuration using the endoscope, the OCT, the PAT, or an ultrasound wave has been described above, but the probe according to the exemplary embodiments may be applied to various medical imaging apparatuses having a structure using an optical coherence microscopy (OCM). For example, a receiver may include a suitable detection sensor depending on the kind of a signal generated from an object, and an appropriate image signal processing method may be used.

As described above, according to one or more of the exemplary embodiments, the probe and the medical imaging apparatus including the same include a view variable apparatus, and thus scan an object located on the side of the probe, in addition to an object located in front of the probe. Furthermore, the view variable apparatus applied to the probe has a very simple mechanical structure, and, for example, may be provided in a probe body having a diameter of several mm or less. Therefore, the view variable apparatus may be used to observe a very narrow part such as a cardiovascular vessel. Accordingly, the exemplary probe and the medical imaging apparatus including the same may be applied to various kinds of organs.

The foregoing exemplary embodiments and advantages are merely exemplary and are not limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A probe comprising:
    a probe body that includes an internal empty space, and is configured to be inserted into a coelom;
    an energy source module that is disposed in the probe body, and configured to emit an energy beam;
    first and second view windows that are provided at an end portion of the probe body, have different fields of view, and are configured to transmit the emitted energy beam; and
    a path changing unit that is disposed in the probe body, and configured to change a traveling path of the emitted energy beam to travel to one of the first view window and the second view window,
    the path changing unit including:
        a reflective plate which is disposed at the end portion of the probe body, is configured to reflect the emitted energy beam by a reflective surface to the first view window by being raised into a slanted position, and is further configured to allow the emitted energy beam to travel to the second view window without being reflected by the reflective surface by being lowered to be substantially parallel to a direction of the emitted energy beam, and
        a slider that is movably disposed in the probe body and includes a distal end to which a proximal edge of the reflective plate is pivotably coupled, and moves a distal edge of the reflective plate to be lowered in a direction perpendicular to the direction of the emitted energy beam when the distal end of the slider moves the proximal edge of the reflective plate in a direction away from the end portion of the probe body.

2. The probe of claim 1, wherein the path changing unit further comprises:
    a guide member configured to restrict movement of the reflective plate according to movement of the slider and guide the reflective plate to one of the slanted position in which the traveling path of the emitted energy beam is directed to the first view window, and a lowered position in which the traveling path of the emitted energy beam is directed to the second view window.

3. The probe of claim 2, wherein the energy source module is disposed to emit the energy beam toward an outside of the end portion of the probe body,
    the first view window is disposed at a side surface of the end portion of the probe body,
    the second view window is disposed at a front surface of the end portion of the probe body,
    the slanted position is an arrangement in which the reflective plate is raised up to be inclined with respect to the slider, and
    the lowered position is an arrangement in which the reflective plate is lowered down to be substantially parallel with the slider.

4. The probe of claim 3, wherein the slider and the reflective plate are coupled to each other by a hinge.

5. The probe of claim 3, wherein the slider and the reflective plate are coupled to each other by an elastic member.

6. The probe of claim 5, wherein the slider, the reflective plate, and the elastic member are provided as one body.

7. The probe of claim 5, wherein the reflective plate is disposed in the slanted position due to elastic-restoring force without external force being applied to the elastic member,
    the guide member exposes the reflective plate without the external force being applied thereto when the distal end of the slider moves toward the end portion of the probe body, and
    the guide member guides the reflective plate to the lowered position with the external force being applied thereto when the distal end of the slider moves in the direction away from the end portion of the probe body.

8. The probe of claim 2, wherein the guide member comprises:
    a first guide member that is disposed at a rear surface of the reflective plate, and guides the reflective plate to the slanted position when the distal end of the slider moves toward the end portion of the probe body; and
    a second guide member that is disposed proximate the reflective surface of the reflective plate, and guides the reflective plate to the lowered position when the distal end of the slider moves in the direction away from to the end portion of the probe body.

9. The probe of claim 8, wherein the path changing unit further comprises a loading member configured to erect the reflective plate to a certain the slanted position.

10. The probe of claim 1, further comprising a driver that is disposed inside or outside the probe body, and configured to move the slider.

11. The probe of claim 1, wherein the first and second view windows are separated from each other, or are continuously provided to form a single window.

12. The probe of claim 1, wherein the energy source module comprises an optical fiber configured to transfer light, which is emitted from a light source disposed outside the probe body, to the end portion of the probe body.

13. The probe of claim 12, wherein the light source comprises a laser configured to emit a pulse laser beam that induces an ultrasound wave from an object, and
    the energy source module further comprises an ultrasound transducer configured to detect the ultrasound wave generated by the object.

14. The probe of claim 1, wherein the energy source module comprises:
    an ultrasound transducer configured to convert an electrical signal into an ultrasound wave, emit the ultrasound wave, and detect the ultrasound wave reflected from an object.

15. The probe of claim 1, wherein the probe body has a longitudinal axis extending in a lengthwise direction of the probe body, the reflective plate is disposed between the energy source module and the second view window along the longitudinal axis, and the first view window is disposed directly above the reflective plate.

16. A medical imaging apparatus comprising:

an energy source configured to emit an energy beam;

a probe which is configured to be inserted into a coelom to transmit the emitted energy beam onto an object and comprises first and second view windows having different fields of view;

a path view changing unit the controller configured to control a path changing unit inside the probe so that a traveling direction of the emitted energy beam is changed to one of the first view window and the second view window;

a receiver configured to receive a signal which is generated from the object in response to the energy beam impinged thereon; and a signal processor configured to process the received signal and generate an image, wherein the path changing unit includes:

a reflective plate which is disposed at an end portion of the probe, is configured to reflect the emitted energy beam by a reflective surface to the first view window by being raised into a slanted position, and is further configured to allow the emitted energy beam to travel to the second view window without being reflected by the reflective surface by being lowered to be substantially parallel to a direction of the emitted energy beam, and a slider that is movably disposed in the probe and includes a distal end to which a proximal edge of the reflective plate is pivotably coupled, and moves a distal edge of the reflective plate to be lowered in a direction perpendicular to the direction of the emitted energy beam when the distal end of the slider moves the proximal edge of the reflective plate in a direction away from the end portion of the probe.

17. The medical imaging apparatus of claim 16, wherein the energy source comprises a light source configured to emit light.

18. The medical imaging apparatus of claim 17, wherein the signal processor is configured to generate an endoscopic image by using the light reflected from the object.

19. The medical imaging apparatus of claim 17, further comprising an optical coherence system configured to split the light emitted from the light source to generate a reference beam and a measurement beam which is coherent light, wherein the signal processor is configured to generate an optical coherence tomography image by using the measurement beam, reflected or scattered from the object, and the reference beam.

20. The medical imaging apparatus of claim 17, wherein the light source comprises a pulse laser configured to induce an ultrasound wave from the object, the receiver is configured to convert the ultrasound wave, generated by the object, into an electrical signal, and the signal processor is configured to generate a photoacoustic image by using the electrical signal.

21. The medical imaging apparatus of claim 16, wherein the energy source and the receiver are embodied as a single ultrasound transducer configured to convert a first electrical signal into an ultrasound wave, emit the ultrasound wave to the object, detect the ultrasound wave reflected from the object, and convert the detected ultrasound wave into a second electrical signal, and the signal processor is configured to generate an ultrasound image by using the second electrical signal.

* * * * *